United States Patent [19]

Watts, Jr. et al.

[11] 4,413,156

[45] Nov. 1, 1983

[54] MANUFACTURE OF SYNTHETIC LUBRICANT ADDITIVES FROM LOW MOLECULAR WEIGHT OLEFINS USING BORON TRIFLUORIDE CATALYSTS

[75] Inventors: Lewis W. Watts, Jr.; Edward T. Marquis, both of Austin, Tex.

[73] Assignee: Texaco Inc., White Plains, N.Y.

[21] Appl. No.: 371,742

[22] Filed: Apr. 26, 1982

[51] Int. Cl.$^3$ ............................................. C07C 5/00
[52] U.S. Cl. ..................................... 585/254; 585/10; 585/255; 585/525; 585/18
[58] Field of Search ..................... 585/10, 12, 18, 255, 585/510, 512, 520, 522, 525, 526, 532, 643, 648, 660, 664, 254

[56] References Cited

U.S. PATENT DOCUMENTS

| | | | |
|---|---|---|---|
| 3,152,998 | 10/1964 | Moss | 252/470 |
| 3,726,938 | 4/1973 | Berger | 585/314 |
| 4,045,508 | 8/1977 | Cupples et al. | 585/511 |
| 4,167,534 | 9/1979 | Petrillo et al. | 585/255 |
| 4,218,330 | 8/1980 | Shubkin | 585/255 |

*Primary Examiner*—Curtis R. David
*Attorney, Agent, or Firm*—Jack H. Park; Kenneth R. Priem; David L. Mossman

[57] ABSTRACT

An improved process for the manufacture of synthetic lubricant additives from olefins having two or three carbon atoms is described. The low molecular weight olefins are converted to internal olefins having 9 to 24 carbon atoms via isomerization and disproportionation. The process utilizes boron trifluoride catalysis with a promoter to produce from the $C_9$–$C_{24}$ internal olefins oligomer mixtures that have surprisingly low viscosities at low temperatures and surprisingly high viscosity indexes as compared with the oligomers found in other methods. It is important that internal olefins be used almost exclusively in the second step of the method of this invention.

17 Claims, No Drawings

MANUFACTURE OF SYNTHETIC LUBRICANT ADDITIVES FROM LOW MOLECULAR WEIGHT OLEFINS USING BORON TRIFLUORIDE CATALYSTS

CROSS-REFERENCE TO RELATED APPLICATIONS

This application is related to co-pending patent application Ser. No. 372,492, filed of even date, which is related to the manufacture of synthetic lubricant additives over boron trifluoride from mixtures of $C_9$–$C_{24}$ olefins comprising greater than 99 weight percent of the mixture, with no limitation on the source of the internal olefins.

This application is also related to co-pending patent application Ser. No. 372,367, filed of even date, which is concerned with a process for making synthetic lubricants via boron trifluoride from paraffins which have been dehydrogenated.

BACKGROUND OF THE INVENTION

1. Field of the Invention

The invention relates to processes for the production of oligomers from low molecular weight olefins, and more particularly relates to the production of internal olefins having 9 to 24 carbon atoms by means of isomerization and disproportionation of olefins having 3 and/or 4 carbon atoms, where the internal olefins are oligomerized by means of a boron trifluoride catalyst.

2. Description of Related Methods

Friedel-Crafts catalysts have long been known to oligomerize olefins. For example, see U.S. Pat. No. 3,410,925 to Eby, et al. in which olefins are mixed with alkylatable aromatic hydrocarbons over a Friedel-Crafts catalyst to form an alkylation sludge which is then mixed with olefins having 3 to 18 carbon atoms which are also passed over the catalyst to produce olefin dimers. U.S. Pat. No. 3,652,706 to Saines, et al. describes the polymerization of olefins having 2 to 20 carbon atoms over a Friedel-Crafts metal halide catalyst plus a hydrogen form of mordenite to produce compounds having a molecular weight between 700 and 2,500. Production of a gasoline fuel composition is described in U.S. Pat. No. 3,749,560 to Perilstein which occurs by reacting a mixture of mono olefins (greater than 50 weight percent alpha olefins) over a Friedel-Crafts catalyst heated to a temperature around 145° C. to produce oligomers having molecular weights between 350 to 1,500. Also, U.S. Pat. No. 3,149,178 to Hamilton, et al. reveals an improved method for making polymerized olefin synthetic lubricants via a particular distillation technique of oligomers made from alpha mono olefins using a Friedel-Crafts catalyst. Alpha olefins having six to twelve carbon atoms may be dimerized in the presence of a Friedel-Crafts catalyst according to the method described in U.S. Pat. No. 4,172,855 to Shubkin, et al.

It is also known that the term "Friedel-Crafts catalysts" includes boron trifluoride among other metal halide-type Lewis catalysts, see *Kirk-Othmer Encyclopedia of Chemical Technology*, Third Edition, Vol. 11, pg 292. Boron trifluoride has also been known to polymerize olefins, as seen in F. Albert Cotton, et al., *Advanced Inorganic Chemistry: A Comprehensive Text*, Interscience Publishers, 1962, p. 191.

A number of U.S. patents have also used $BF_3$ to oligomerize olefins. Close study will reveal that alpha olefins are considered the only useful form. For example, U.S. Pat. No. 2,780,664 to Serniuk describes the reaction of conjugated dienes with mono alpha and internal olefins over $BF_3$ promoted by an ether mixed with a halo alkane diluent at a temperature from −30° to 100° C. to produce oligomers suitable for drying oils. Alpha olefins having from 5 to 20 carbon atoms are oligomerized using $BF_3$ plus an alcohol or water promoter as described in U.S. Pat. No. 3,382,291 to Brennan. In this patent, $BF_3$ and a mixture of $BF_3$ plus the promoter complex are introduced in two separate streams. Another U.S. patent by Brennan, U.S. Pat. No. 3,742,082, concerns the dimerization of alpha olefins via $BF_3$ which is promoted with phosphoric acid or water at a temperature from 100° to 150° C. U.S. Pat. No. 3,763,244 to Shubkin, which describes the oligomerization of n-alpha olefins having 6 to 16 carbon atoms over $BF_3$ promoted with water, at a temperature between 10° and 60° C. where it is preferred that $BF_3$ is added continuously.

Yet another U.S. patent to Brennan, U.S. Pat. No. 3,769,363, describes the oligomerization of olefins having 6 to 12 carbon atoms using $BF_3$ with a carboxylic acid promoter having at least 3 carbon atoms at a temperature between 0° and 20° C. to produce olefins heavy in trimer form. U.S. Pat. No. 3,780,128 also to Shubkin relates to the oligomerization of alpha olefins having 6 to 16 carbon atoms in which $BF_3$ is employed in a molar excess of alcohol. U.S. Pat. No. 3,876,720 to Heilman, et al. describes a two-step procedure by which alpha olefins having 8 to 12 carbon atoms are converted to vinylidene olefins which are then reacted over a 1:1 molar complex of $BF_3$ and alcohol to produce oligomerized vinylidene olefins. A method for oligomerizing both short and long chain alpha olefins having from 14 to 20 carbon atoms simultaneously over $BF_3$ with an alcohol or water promoter at 0° to 60° C. with a monomer recycle is described in U.S. Pat. No. 4,225,739 to Nipe, et al. There is also U.S. Pat. No. 4,263,465 to Sheng, et al. which describes a two-step process for reacting one-butene with a higher alpha olefin over $BF_3$ in the presence of a proton donor at a temperature from −30° to 50° C. to produce an oligomer having 8 to 18 carbon atoms. The intermediate oligomer is reacted with other higher alpha mono olefins over the same catalyst system from −30° to 60° C. to produce oligomers having 20 to 40 carbon atoms. For more information on $BF_3$-catalyzed oligomerization of alpha olefins, see Brennan, "Wide-Temperature Range Synthetic Hydrocarbon Fluids," Ind. Eng. Chem. Prod. Res. Dev. 1980, Vol. 19, pp 2–6 and Shubkin, et al., "Olefin Oligomer Synthetic Lubricants: Structure and Mechanism of Formation," Ind. Eng. Chem. Prod. Res. Dev. 1980, Vol. 19, pp 15–19.

Two patents have been located which involve the reaction of internal olefins over Friedel-Crafts catalysts. U.S. Pat. No. 4,167,534 to Petrillo, et al. describes olefins which are both alpha and internal having from 10 to 15 carbon atoms which are reacted over Friedel-Crafts catalysts between 20° and 200° C. to produce oligomers. The catalysts used in the examples of this patent are only $AlCl_3$ and $NaAlCl_4$. The internal olefins are also those that are statistically distributed. Also, the oligomers found useful therein seem to be the hydrogenated bottoms product after the unreacted olefins are removed, without further distillation. U.S. Pat. No. 4,218,330 to Shubkin describes hydrogenated dimers from alpha olefins having from 12 to 18 carbon atoms, especially 1-tetradecene, made using a Friedel-Crafts catalyst, which includes therein boron trifluoride with a promoter. Shubkin's method uses predominantly alpha olefins, although the specification mentions that "fairly large amounts of internal olefins can be tolerated without adversely affecting the physical properties of the oligomer." This last remark from Shubkin reveals the general feeling of those working in the field that internal olefins do not produce oligomers with good properties for synthetic lubricants. For example, in U.S. Pat. No. 3,952,071 to Isa, et al., it is revealed that olefins may be oligomerized in the presence of a mixture of a polyhydric alcohol derivative and an aluminum halide. Isa, et al. mention that the olefin could be internal or alpha although alpha olefins are the only ones used in the examples therein. U.S. Pat. No. 3,947,509, also to Isa, et al., also claims that internal olefins may be used over a ketone and ester ether or alcohol promoted aluminum chloride catalyst although only alpha olefins are used in the examples.

U.S. Pat. No. 4,300,006 issued on Nov. 10, 1981. It describes a process for producing a hydrocarbon oil by contacting a mixture of alpha and at least 50 weight percent internal olefins with a boron trifluoride dimerization catalyst. However, the productivity of useful products from the process revealed in U.S. Pat. No. 4,300,006 is quite low. For example, an alkane diluent is found to be necessary in the process described therein which, in addition to distilling out the lights and the heavies to obtain the lube oil, results in little useful product. Further, this method requires a much longer reaction time and a higher catalyst concentration than desired. It would be beneficial if a method for producing synthetic lubricant components could be devised which would overcome the aforementioned disadvantages.

With regard to the first step in the method described herein, many other researchers have devised schemes for isomerizing or disproportionating olefins, occasionally applying both techniques. For example, in an article entitled "Butylene & ethylene (Triolefin process)" attributed to Phillips Petroleum Company in *Hydrocarbon Processing*, November, 1981 page 141, a method is described for converting propylene to ethylene and butylene via disproportionation. E. R. Freitas, et al. in Shell Chemical Company Technical Bulletin SC:335-79 entitled "Shell Higher Olefins Process—SHOP" presented at the AICHE 85th National Meeting, June, 1978, reveal how ethylene may be upgraded to $C_{10}$–$C_{20}$ alpha olefins via oligomerization and $C_{11}$–$C_{14}$ internal olefins via isomerization and disproportionation of alpha olefins smaller than $C_{10}$ and larger than $C_{20}$.

U.S. Pat. No. 3,647,906 to Shell Oil Company appears to be part of the SHOP technology described in the previously cited bulletin. The patent encompasses a method by which ethylene is converted to linear alpha olefins via oligomerization, isomerization and disproportionation. Suitable oligomerization catalysts are listed as Ziegler-type catalysts; i.e., compounds of metals such as alkali metals; e.g., lithium, sodium, potassium; alkaline earth metals such as beryllium and magnesium; and Group III metals such as aluminum, gallium and iridium. Phosphorous-containing bidentate ligands, especially nickel chelates thereof are found to be useful ethylene oligomerization catalysts. Suitable isomerization catalysts are listed as being supported phosphoric acid, bauxite, alumina supported cobalt oxide, iron oxide or manganese oxide. Preferred disproportionation catalysts are rhenium oxides supported on alumina, especially those which have been pre-treated with alkali or alkaline earth metal compounds. Also listed are catalysts useful for the simultaneous isomerization and disproportionation such as $MoO_3$/$CoO$/$MgO$ on alumina and $Re_2O_7$/$K_2O$ on alumina.

Another process for converting ethylene to linear mono olefins via oligomerization, isomerization and disproportionation is outlined in U.S. Pat. No. 3,726,938. The only catalysts listed which are different from those mentioned in U.S. Pat. No. 3,647,906, described above are the disproportionation catalysts of molybdenum and tungsten supported on inorganic carriers such as alumina or silica.

In the field of oligomerizing olefins for synthetic lubricants, it is a continual problem to produce olefins having low viscosities at room temperature and below but which have a high viscosity index and low volatility.

SUMMARY OF THE INVENTION

The invention relates to a process for converting $C_3$–$C_4$ linear olefins to a synthetic lubricant component comprising
a. isomerizing a linear olefin feedstock selected from the group of olefins consisting of propylene, butene-1, butene-2 and mixtures thereof, over a suitable heterogeneous isomerization catalyst under suitable isomerization conditions,
b. disproportionating the mixture resulting from the isomerization step by passing the mixture over a suitable heterogeneous disproportionation catalyst under suitable disproportionation conditions,
c. separating from the mixture resulting from the disproportionation step a mixture of olefins having carbon numbers ranging from 9 to 24, and being comprised of 99 weight percent or more internal olefins,
d. oligomerizing the mixture of internal olefins separated in the previous step by contacting the mixture with a catalyst comprising boron trifluoride under conditions sufficient to effect oligomerization of said olefins,
e. mildly stripping off any unreacted olefin monomers from the mixture of oligomerized olefins resulting from the oligomerization step, and
f. hydrogenating the oligomerized olefins from the previous step in the presence of hydrogen and a hydrogenation catalyst to produce a synthetic lubricant component.

DESCRIPTION OF THE PREFERRED EMBODIMENTS

It has been surprisingly discovered that oligomers which have an unusual blend of properties may be made by reacting predominantly internal mono olefins with boron trifluoride and a promoter. The internal mono olefins are made by isomerizing and disproportionating propylene, 1-butene, 2-butene and mixtures thereof. It is believed that this is the first time internal olefins have been proposed to be made by both isomerizing and disproportionating a feedstock limited to such a narrow carbon number range. It is also important to note that predominantly internal olefins are employed in the oligomerization step of this invention.

Isomerization/Disproportionation Step

The raw materials for the first step of the inventive process are inexpensive, abundant by-products of ethylene production; i.e., propylene, 1-butene, 2-butene and mixtures thereof. The method does not employ the higher valued downstream ethylene products such as alpha olefins. The utilization of these ethylene by-products which are also available from catalytic cracking units, as precursors of internal olefins suitable for the synthesis of synthetic lubricants represents a departure from the known conversion of propylene to products such as ethylene and butene-2 and the transformation of high and low alpha olefins to mixed internal olefins discussed previously.

The preferred initial raw materials in this process are propylene, butene-1, butene-2 or mixtures thereof, essentially free of both allene and butadiene and low in isobutylene. Although economic considerations discourage cofeeding substantial amounts of such inert diluents as paraffins, such materials may be present without adversely affecting the reactions if so desired by one skilled in the art.

EXAMPLE A

In a typical example, the feedstock will be butene-2 isolated or "concentrated" upon distillation of butene-1 from a steam pyrolysis, butadiene and isobutylene-extracted $C_4$ stream.

This essentially water-free stream will be isomerized in the presence of catalysts capable of effecting doublebond isomerization of olefins without promoting extensive carbon-carbon bond isomerization, such as converting butene to isobutylene. Suitable catalysts that would be used include cobalt oxide, iron oxide or manganese oxide on alumina and also sodium-potassium carbonate on gamma alumina. The preferred catalyst would be the sodium and potassium carbonate combination supported on gamma alumina. The isomerization will be conducted in the liquid phase at a temperature of about 70° C. in the presence of a gamma alumina support impregnated with sodium and potassium carbonates at a liquid hourly space velocity (LHSV) of about 1.

The resulting mixture will then be subjected to an olefin disproportionation reaction for which many versions are well known. A suitable heterogeneous disproportionation catalyst to be employed will be taken from the group of molybdenum, tungsten or rhenium on alumina supports and mixtures of molybdenum and cobalt on alumina. Reaction conditions will include a temperature in the range of about 100 to 175° C., a LHSV of about 1 to 3 and a pressure of greater than 200 psig. The ethylene that is produced will be removed and the remaining reaction mixture will be recycled to the disproportionation reaction. This procedure will be repeated until economically acceptable concentrations of $C_9$–$C_{24}$ internal olefins, in general, are produced. As will be seen, a particularly preferred feedstock for the second step of this process is a $C_{13}$–$C_{14}$ internal olefin mixture. In this case, the disproportionation reaction would be designed to concentrate $C_{13}$–$C_{14}$ internal olefins in the product stream.

The desired carbon range will be isolated by distillation, extraction and other separation techniques. The remaining olefins will be recycled to extinction or alternatively, mixed with fresh feed and recycled. Paraffins, and perhaps highly branched olefins, will be optionally purged.

Oligomerization Step

Generally, the olefins used as the feed to this step should have between 9 and 24 carbon atoms, inclusive. The internal olefins used herein should have the double bond randomly distributed across the molecule. In this context the term "randomly distributed" means that the double bond in the internal olefin is not predominantly in any one location. For example, an olefin mixture being comprised of a majority of alpha olefins would be outside the scope of this definition since the double bond would be located predominantly between the first and second carbon atoms of the molecules. Likewise, since the internal olefins used for oligomerization in the method of U.S. Pat. No. 4,300,006 are made by disproportionation of alpha olefins, the double bond is located predominantly at or near the center of the molecule, and such olefin feedstocks also fall outside the definition of having a "random distribution" of the double bond. A random distribution includes the distribution one may obtain upon the dehydrogenation of paraffins or on isomerizing and disproportionating low molecular weight olefins. One would expect a small amount of alpha olefin to result from such a distribution. However, one would also anticipate that the alpha olefin proportion would be only about 0.1 weight percent, with a maximum value being about 1.0 weight percent. The double bond would appear in all possible positions. As a practical matter, the feedstocks herein can be considered to be entirely internal olefins. The internal olefins may be generally expressed as compounds having the formula $RCH=CHR'$ where R and R' are the same or different alkyl radicals of one to twenty-one carbon atoms. However, the total number of carbon atoms should not exceed about twenty four and should not be less than nine. The internal olefin mixtures are potentially more available than the pure cut alpha olefins and are potentially as cheap or cheaper than the corresponding pure cut alphas used in practically all other oligomerization methods. It will be shown that the method of this invention affords higher quality products and higher conversions than those obtained with $AlCl_3$ and $AlCl_4Na$ catalysts.

By careful selection of the molecular weight of the feed olefins and the reaction conditions, it was found that a synthetic lubricant base oil with a specific viscosity can be made by the method of this invention which has superior properties over those made by other methods. For example, it has been found that a base oil having a 210° F. viscosity of about 4 centistokes with excellent properties can be made with internal olefins having 13 or 14 carbon atoms. A "four centistoke fluid" is a designation given to fluids used in lubricating oil compositions which generally have 210° F. viscosities of about 4 centistokes. It is anticipated that "six centistoke fluids" as well as fluids with other viscosities may be made by one skilled in the art using the method of this invention.

The catalyst of choice is boron trifluoride. A number of different kinds of promoters may be used, such as alcohols, carboxylic acids or water. It is especially preferred that 1-butanol be used as the promoter. The temperature range at which the oligomerization may be performed successfully is between 25° and 150° C., with an especially preferred range between 65° to 105° C. The pressure range of the reaction may run from atmospheric to 1000 psig. The oligomerization of the olefins may be conducted in a batch or continuous mode. First, the experimental methods will be described, and then the results will be tabulated.

COMPARATIVE EXAMPLES

A number of comparative oligomerization examples were run using the procedures of U.S. Pat. No. 4,167,534, the disclosure of which is incorporated by reference herein. It is believed that this patent constitutes the closest prior art. The examples herein were patterned after Examples 1, 5 and 7 therein. These examples were chosen because they represented a wide variety of conditions, particularly temperature. The primary variable in the comparative examples is the olefin feed material, although sometimes twice the amount of $AlCl_3$ used in the U.S. Pat. No. 4,167,534 patent is employed in an attempt to improve the conversion.

According to the disclosure in U.S. Pat. No. 4,167,534, Example 1 is begun by heating the feedstock to 80° C. The feedstock is then added over 15 minutes with 1% $AlCl_3$. The temperature is then raised to 100° C. and maintained for 100 minutes. The product is then discharged, separated from the heavy catalytic layer, washed with caustic solution and then distilled.

Example 5 begins by adding the olefin feed at room temperature with 1% $AlCl_3$ in only one portion. the temperature is allowed to rise on its own for 120 minutes. The product is then discharged, separated from the heavy catalytic layer, washed with caustic solution and distilled.

The feed in Example 7 of U.S. Pat. No. 4,167,534 is added at 130° C. with 5% $NaAlCl_4$ over 90 minutes. The reaction mass is then maintained at 130° C. for 60 minutes further. The product is then discharged, separated from the heavy catalytic layer, washed with caustic solution and distilled. The results of the comparative examples are shown in Table I.

employed in the examples of Table I for comparative purposes.

Viscosities at two strandard temperatures are given in centistokes. The viscosity index (VI) is the change in viscosity with temperature such that the higher the number, the lower is the change in viscosity with temperature. Conversely, a low VI signifies a large change in viscosity with temperature. Pour point is a measure of the temperature, in degrees Farenheit, at which the sample will begin to pour. Below that temperature the composition may generally be regarded as a solid. The thermogravimetric analysis (TGA) is a measure of volatility via measuring the weight percent of sample remaining at 233° C. as the temperature is raised in a slow, uniform manner, usually 10° C. per minute. An oligomer product should have a TGA analysis with at least 80% of the sample remaining at 233° C. in order to have sufficiently low volatility to be useful as a base stock for lube oil formulation. A good oligomer mixture has a less than 10% distillation loss at about 700° F.

EXAMPLES ILLUSTRATING THE INVENTION

The following examples illustrate the method of the invention using $BF_3$ as the catalyst and as the olefin feed, only internal olefins which would be created by the isomerization and disproportionation of linear $C_3$-$C_4$ olefins as described earlier. Two examples are included using $C_{14}$ alpha olefin as the feedstock to show that an unsuitable oligomer mixture is produced. The oligomer from alpha olefins having 14 carbon atoms (1-tetradecene) was deficient in its low temperature properties. Generally, the viscosity at 25° C. should be 30 to 30.5 centistokes (cs) or less while the $C_{14}$ alpha olefin olgimer was observed to be in the 32-33 cs range. These differences are exaggerated at −30° C. (the temperature at which cold cranking viscosity tests are done) and would result in a too viscous fluid at cold temperatures.

Preferably, a "4 centistoke fluid" (measured at 210°

TABLE I
COMPARATIVE EXAMPLES

| | Reaction Conditions | | Temperature °C. | Method of U.S. Pat. No. 4,167,534 Used | Conversion Basis LC | % Bottoms Basis Olefin Charged | Properties of Hydrogenated Stripped Oligomer | | | | |
|---|---|---|---|---|---|---|---|---|---|---|---|
| | | | | | | | Viscosity, centistokes, | | | Pour Point, °F. | TGA: % Sample Remaining at 233° C. |
| Example | Feed | Catalyst | | | | | 210° F. | 25° C. | VI | | |
| 1 | $C_{13-14}$ int. | $AlCl_3$ | 80 | Ex. 1 | 32.5 | 21.6 | 5.69 | 56.00 | 125.4 | −50 | 91.8 |
| 2 | $C_{13-14}$ int. | $AlCl_3$* | 80 | Ex. 1 | 42.2 | 29.2 | 5.85 | 60.96 | 121.4 | <−50 | 91.3 |
| 3 | $C_{11-14}$ int. | $AlCl_3$ | 80 | Ex. 1 | | 21.0 | 6.79 | 80.39 | 116.9 | <−50 | 88.5 |
| 4 | $C_{14}$ alpha | $AlCl_3$ | 80 | Ex. 1 | 85.9 | 80.2 | 22.07 | 341.83 | 129.9 | +20 | 98.2 |
| 5 | $C_{13-14}$ int. | $AlCl_3$ | R.T.** | Ex. 5 | 24.8 | 16.8 | 6.40 | 68.90 | 124.4 | −50 | 92.2 |
| 6 | $C_{13-14}$ int. | $AlCl_3$* | R.T. | Ex. 5 | 45.6 | 27.4 | 6.43 | 71.75 | 122.1 | <−50 | 91.4 |
| 7 | $C_{11-14}$ int. | $AlCl_3$ | R.T. | Ex. 5 | 36.8 | 23.2 | 7.12 | 86.72 | 116.5 | <−50 | 89.5 |
| 8 | $C_{14}$ alpha | $AlCl_3$ | R.T. | Ex. 5 | 93.9 | 87.6 | 18.20 | 260.91 | 131.2 | +10 | 98.3 |
| 9 | $C_{13-14}$ int. | $NaAlCl_4$ | 130 | Ex. 7 | 42.0 | 30.3 | 5.20 | 48.68 | 125.9 | <−50 | 88.2 |
| 10 | $C_{11-14}$ int. | $NaAlCl_4$ | 130 | Ex. 7 | 68.9 | 44.8 | 6.96 | 87.04 | 114.0 | −45 | 91.3 |
| 11 | $C_{14}$ alpha | $NaAlCl_4$ | 130 | Ex. 7 | 100.0 | 87.1 | 19.44 | 286.80 | 130.5 | +15 | 96.0 |

*Twice as much $AlCl_3$ was used in these examples as described in the examples of U.S. Pat. No. 4,167,534
**R.T. means room temperature With respect to the results outlined in Table I, the conversion is a weight percent of monomer oligomerized as determined by liquid chromatography. The weight percent of the bottoms as based on the olefin charged is given in the next column. While these two columns of data generally measure the same concept (notice the qualitative correlation), the applicants prefer to use "% conversion" while the inventors in U.S. Pat. No. 4,167,534 used the "% bottoms" method. Both are F.) should have a viscosity between 25 and 40 centistokes at 25° C., a viscosity between 3.5 and 5.0 centistokes at 210° F., a viscosity index of greater than 100 and a thermogravimetric analysis value of greater than 80 weight percent.

EXAMPLE 12

A solution of 43.8 g $C_{13-14-15}$ random internal linear olefins (53.4% $C_{13}$, 45.0% $C_{14}$, 0.5% $C_{15}$, 1.1% paraffins) and 0.12 g 1-butanol in a nitrogen atmosphere was saturated with $BF_3$ at 25° C. by slow sparging for 25 minutes. Pot contents were mantained at 25°–27° C. by external cooling while 55.6 g of a solution of 55.0 g $C_{13-14-15}$ olefins and 0.8 g 1-butanol was added over 1⅝ hours. Boron trifluoride saturation was maintained during this addition and for 1¾ hours thereafter. Boron trifluoride introduction was stopped and the pot contents were heated to 86° C. over a 1¾ hour period, and maintained at 85°–86° C. for ½ hour. After cooling, 110 ml $H_2O$ was added; the contents were stirred rapidly for 20 minutes, and the top layer was removed. It was washed with 115 ml $H_2O$ and stripped on a rotary evaporator at 30 mm Hg to a maximum bath temperature of 95° C.; 96.9 g of a clear light yellow liquid remained (98.3% recovery). Analysis by gel permeation chromatography indicated 61.34% dimer, 25.13% trimer, and 12.95% monomer.

EXAMPLE 13

The product of Example 12 (93.8 g) was hydrogenated over 9.60 g of a powdered Ni/Cu/Cr catalyst, which is described in U.S. Pat. No. 3,152,998, incorporated by reference herein. The conditions included a pressure of 1800 psig $H_2$ and a temperature of predominantly 208° C. (with temperature briefly reaching 316° C.).

After vacuum stripping at 0.9 mm Hg to remove 11.89 g of lighter components (>91% monomers), the hydrogenated bottoms product consisted (GPC analysis) of 26.7% trimer, >67.8% dimer, and >3.41% monomer. The kinematic viscosities at 25° C., 100° F., and 210° F. were 29.57, 18.26 and 3.89 centistokes, respectively. The pour point was measured to be less than −50° F. Thermogravimetric analysis indicated 81.3% of the sample remained at 233° C. As a result, this material is too volatile for synthetic lubricant use.

EXAMPLE 14

This is essentially the same procedure as Example 12 except $BF_3$ introduction was stopped when olefin/1-butanol introduction stopped. The heating period was for 2 hours at 90° C. GPC analysis indicated 19.8% trimer, 62.2% dimer and 17.94% monomer.

Hydrogenation

In order to form materials which have adequate oxidative stability for lubricants, the oligomerized olefins are optionally hydrogenated either partially or totally. This hydrogenation is done by procedures known to those skilled in the art as exemplified by U.S. Pat. No. 4,045,508; U.S. Pat. No. 4,013,736; U.S. Pat. No. 3,997,622 and U.S. Pat. No. 3,997,621. A particularly preferred catalyst for this hydrogenation is a nickel-copper-chromia catalyst described in U.S. Pat. No. 3,152,998, incorporated by reference herein. As is well known, such hydrogenations may be performed in either batch or continuous modes.

When the instant inventive method was scaled up for a pilot plant run, it was discovered that the resulting oligomer mixture did not give the expected desirable properties seen in the lab scale experiments. In the pilot plant scale-up, stripping out the monomer was performed first and then hydrogenation was conducted over the nickel-copper-chromia catalyst described above. Monomer removal was performed before hydrogenation and recycled to the oligomerization step. However, during the pilot plant stripping step over 50% of the oligomer material came off overhead at temperatures starting at about 210° C. to about 282° C. at the finish in an attempt to obtain a material with a good TGA (volatility) value. Apparently, some of the unhydrogenated oligomer mixture was thermally unstable and portions of it were reverting to monomers or intermediates and distilling off as volatiles. It is, therefore, important that monomer removal be accomplished at as mild conditions as possible; that is, the reboiler or pot temperatures should preferably be kept at or under 180° C. when stripping out monomer.

While the methods of others in the field include a distillation step after hydrogenation procedure to obtain products of various 210° F. viscosities, it is much preferred in the method of the invention that no further distillation be conducted. In other words, the monomer-stripped, hydrogenated bottoms are the desired synthetic lubricant components. Thus the method of this invention does not require the customary distillation step, yet surprisingly produces a synthetic lubricant component that has excellent properties and performs in a superior fashion. However, it is also anticipated that one skilled in the art may find subsequent distillation useful in the practice of the method of this invention.

EXAMPLES 15–26

The following examples illustrating the method of the invention were conducted according to one of the following procedures.

Procedure A

Examples 15 through 18 used the following experimental procedure. To a 300 ml stainless steel clave (316 SS) was charged 158.6 g of olefin and 1.4 g of 1-butanol. The clave was sealed and heated to approximately 98° C. at which time $BF_3$ gas was introduced in amounts ranging from 3.1 to 4.4 g (average 3.8 g $BF_3$ per run). The reaction was stirred and allowed to exotherm on its own (no cooling). The reaction was stirred for 60 minutes (time measured from first $BF_3$ addition and $BF_3$ added over a 3–6 minute period) and then cooling water turned on. The cool reaction mixture was neutralized with 10 grams of $Na_2CO_3$ and 100 ml $H_2O$. After layer separation, the organic layer was washed twice more with fresh water and dried. The oligomer was analyzed (GPC/LC) for conversion and subjected to hydrogenation at 210° C. (2 hours), 2,000 psig $H_2$ pressure in the presence of a nickel-copper-chromium oxide catalyst (5% by weight basis weight oligomer).

Procedure B

Examples 19 through 23 used procedure B which was identical to Procedure A except that 0.7 g butanol was used (instead of 1.4 g) and the amount of $BF_3$ added ranged from 2.2 to 2.8 g with a 2.5 g average.

Procedure C

Examples 24 through 26 used Procedure C which was identical to Procedure A except that the temperature of the reaction mixture (olefin and promoter) before $BF_3$ addition was 65° C. (instead of 98° C.) and the amount of $BF_3$ added ranged from 2.2 g to 4.0 g (3.0 g average). Conversions and properties of the oligomers are summarized in Table II.

It should be noted that the amount of catalyst used in the method of this invention (1.4 to 2.8 weight percent of the olefin feed) is notably less than the amount of catalyst used in other methods in the field, such as the method disclosed in U.S. Pat. No. 4,300,006 (2.6 to 6.1 weight percent). In further contrast with the method of this particular patent, no employment of a diluent, no heavies or lights (except monomers) removed, and a shorter reaction time are features of the inventive method. Another difference lies in the fact that the method of U.S. Pat. No. 4,300,006 uses a mixture of alpha and internal olefins having carbon numbers that are quite different from each other, unlike the instant method.

cal (being formed from the disproportionation of two alpha olefins). For example, Runs IX and XII therein oligomerize $C_{14}$, $C_{16}$ and $C_{18}$ internal olefins where the double bond is at or near the center of the olefin molecule. The inventive method uses instead internal olefins where the double bond is randomly distributed instead of located near the center of a symmetrical mono olefin. These differences in the feedstocks cause important differences in the properties of the resulting oligomers, as shown by the following examples involving $C_{14}$ inter-

TABLE II
EXAMPLES ILLUSTRATING THE INVENTION

| | | | | | | Properties of Hydrogenated Stripped Oligomer | | | | |
|---|---|---|---|---|---|---|---|---|---|---|
| | Reaction Conditions | | Temp., | | | Conversion | Viscosity, centistokes, | | Pour Point, | TGA: % Sample Remaining |
| Example | Feed | Catalyst | °C. | Procedure | | Basis LC | 210° F. | 25° C. | VI | °F. | at 233° C. |
| 15 | $C_{13-14}$ int. | $BF_3$-butanol | 98 | A | | 90.5 | 3.82 | 29.67 | 114.4 | $<-50$ | 89.5 |
| 16 | $C_{11-14}$ int. | $BF_3$-butanol | 98 | A | ⎫ | | | | | | |
| 17 | $C_{11-14}$ int. | $BF_3$-butanol | 98 | A | ⎬ avg. | 83.7 | 4.45 | 40.79 | 106.8 | $<-50$ | 89.2 |
| 18 | $C_{11-14}$ int. | $BF_3$-butanol | 98 | A | ⎭ | | | | | | |
| 19 | $C_{13-14}$ int. | $BF_3$-butanol | 98 | B | | 86.4 | 3.68 | 29.17 | 118.1 | $-30$ | 88.8 |
| 20 | $C_{11-14}$ int. | $BF_3$-butanol | 98 | B | ⎫ | | | | | | |
| 21 | $C_{11-14}$ int. | $BF_3$-butanol | 98 | B | ⎬ avg. | 53.4 | 4.04 | 34.48 | 105.0 | $<-50$ | 84.9 |
| 22 | $C_{11-14}$ int. | $BF_3$-butanol | 98 | B | ⎭ | | | | | | |
| 23 | $C_{14}$ alpha | $BF_3$-butanol | 98 | B | | 89.1 | 4.27 | 33.09 | 134.3 | $-35$ | 98.8 |
| 24 | $C_{13-14}$ int. | $BF_3$-butanol | 65 | C | | 83.4 | 3.86 | 29.90 | 119.4 | $<-50$ | 90.4 |
| 25 | $C_{11-14}$ int. | $BF_3$-butanol | 65 | C | | 77.5 | 5.19 | 52.54 | 115.6 | $<-50$ | 93.8 |
| 26 | $C_{14}$ alpha | $BF_3$-butanol | 65 | C | | 83.6 | 4.41 | 32.70 | 148.6 | $-30$ | 93.5 |

It may be noted from inspection of Tables I and II that alpha olefins produce invariably poorer oligomer mixtures than do internal olefins. No examples have higher viscosities at both 210° F. and 25° C. than do the alpha olefin Examples 4, 8 and 11. It must be remembered that the inventive method herein has the requirement of using only internal olefins to obtain low viscosities, a feature not found in any related method. It should also be pointed out that oligomers made from alpha olefins (Examples 4, 8, 11, 23 and 26) may have rather high pour points, which make them unacceptable for use in synthetic lubricants.

Secondly, it may be noted that the viscosities of the $BF_3$ catalyzed oligomers are all lower than those produced by the method of U.S. Pat. No. 4,167,534. In addition, the conversions are much higher in the $BF_3$ runs. It is particularly surprising that $C_{13-14}$ internal olefins (Examples 15, 19 and 24), having a higher average molecular weight than the $C_{11-14}$ internal olefins (Examples 16-18, 20-22 and 25) produce olefin mixtures having a lower viscosity than the mixtures from $C_{11-14}$ internals. These examples show how the choice of molecular weight range of the olefin feedstock greatly affects the properties of the product oligomers.

It is surprising that such low viscosities (relative to other methods) may be found in oligomer mixtures that also have low pour points and viscosity indexes and volatilities comparable with those of other methods. It is precisely such a blend of advantageous properties that is being sought after in the field and which has not been discovered until now.

In addition, it should be noted that the method revealed in U.S. Pat. No. 4,300,006, incorporated by reference herein, requires that the dimerization feedstock be obtained from the disproportionation of alpha olefins having 8 to 10 carbon atoms. As a result, the dimerization feedstocks therein are a mixture of alpha and internal olefins where the alpha olefins have slightly more than half the carbon number of the corresponding internal olefin and the internal olefins are highly symmetrinal olefin and $C_8$ alpha olefin as a mixed feedstock.

EXAMPLE 27
Oligomerization

The oligomerization of a 70 weight percent $C_{14}$ internal olefin and 30 weight percent $C_8$ alpha olefin mixture was accomplished over 2.5 g of a boron trifluoride catalyst with 1.1 g of 1-butanol as a protonic promoter and initiated at 95.1° C.

To a dry and clean 300 ml Hastelloy C autoclave were added 119 g of $C_{14}$ internal olefin from Shell Chemical Company's Higher Olefin Process (SHOP). The double bond in these internal olefins is randomly distributed throughout the molecule. Added at the same time were 51 g of $C_8$ alpha (1-octene from Aldrich Chemical Company, Inc.). At the time, this was the closest approximation possible of the U.S. Pat. No. 4,300,006 feedstock. These additions were followed by 1.1 g of 1-butanol promoter. The clave was sealed and the contents heated to 95.1° C. with stirring. Starting at 95.1° C., $BF_3$ gas was introduced by adding four shots of $BF_3$ over an 11 minute period (2.5 g total $BF_3$ added) to the stirred reaction mixture. At the end of 17 minutes (measured from the first $BF_3$ addition), the temperature had risen 110.2° C. for a maximum exotherm of 15.1° C. One hour after the first $BF_3$ addition the reaction temperature was 101.5° C. The heat was turned off and cooling water turned on. The reaction mixture was neutralized with an aqueous $Na_2CO_3$ solution and water washed twice more. The organic layer was separated and dried by filtering through folded filter paper to obtain a net weight of 156.3 g. Liquid chromatography analysis indicated 31.9% of the material was $C_8$, $C_{14}$ or $C_{16}$ and 27.5% was dimer $C_{22}$ (from $C_8$ and $C_{14}$) and 32.2% was dimer $C_{28}$ (from $C_{14}$ and $C_{14}$) while 8.3% was $C_{36}$ or heavier. Conversion to material higher than $C_{16}$ was about 68.1%. The ratio of dimer to trimer and heavies was 7.19:1.

Hydrogenation and Stripping

A 1-liter stirred 316 stainless steel clave was charged with 144.5 g of oligomer from the previous step and 7.2 g of a nickel-copper-chromium oxide hydrogenation catalyst. The clave was flushed with hydrogen three or four times and pressured to 1,000 psig with hydrogen. Subsequently, the clave was heated to 210° C. (the pressure increased to only 1,200 psig) and pressurized again to 2,000 psig with hydrogen. The reaction mixture was stirred at 210° C. for four hours during which the pressure remained at 2,000 psig. The hydrogenated oligomer was filtered and 137.3 g subjected to high vacuum stripping. The material was distilled through a jacketed column (with about 12 in. of Goodloe packing) until the head temperature reached 105° C. at 0.06 mm Hg. The bottoms weighed 67.1 g (49.6% of the total material, overhead plus bottoms) and the overhead weighed 68.3 g (50.4% of the total material). The bottoms product had a 210° F. viscosity of 3.6 cs, a 25° C. viscosity of 27.4 cs, a pour point of $<-50°$ F. and a viscosity index of 110. Liquid chromatography analysis indicated the presence of 25.5% dimer ($C_{22}$), 60.2% dimer ($C_{28}$) and 14.3% heavier materials. The TGA of the bottoms product indicated volatility was moderately high (85.0% sample remained at 233° C. in TGA of 10° C./minute).

EXAMPLE 28

Oligomerization

Oligomerization of a 70% $C_{14}$ internal olefin—30% $C_8$ alpha olefin mixture catalyzed by 2.2 g of $BF_3$ with 1.1 g of 1-butanol as a promoter was initiated at 94.9° C. As in the previous example, 119 g of $C_{14}$ internal olefin were added to a 300 ml clave along with 51 g of $C_8$ alpha olefin followed by 1.1 g of 1-butanol. The clave was sealed and heated to 94.9° C. Starting at 94.9° C., $BF_3$ gas was added over an 11 minute period (totalling 2.2 g of $BF_3$) to produce a 15.1° C. maximum exotherm after 16 minutes had elapsed after the first $BF_3$ addition. After a one hour reaction time measured from the first $BF_3$ addition, the mixture was cooled and neutralized with aqueous sodium carbonate. The organic layer was separated and dried by filtering through folded filter paper, to give a net weight of 162.5 g. Liquid chromatography analysis indicated 31.1% of the material was $C_8$, $C_{14}$ or $C_{16}$, 27.2% was dimer $C_{22}$ and 33.4% was dimer $C_{28}$ while 8.3% was $C_{36}$ or heavier. Conversion to materials higher than $C_{16}$ was 68.9%. The ratio of dimer to trimer and heavies was 7.30:1.

Hydrogenation and Stripping

From the above step, 145.0 g of the oligomer was hydrogenated over 7.2 g of nickel-copper-chromium oxide catalyst. The hydrogenation was conducted at 210° C. and 2,000 psig from hydrogen for four hours. It was followed by filtration and stripping as described in the previous example. The bottoms products amounting to 55.3% of the charge had a 25° C. viscosity of 25.7 cs and a 210° F. viscosity of 3.45 cs. The pour point of the bottoms material was $-40°$ F. and the viscosity index was 109.0. Liquid chromatography analysis indicated 33.6% dimer $C_{22}$ and 53.8% dimer $C_{28}$ and 12.6% heavies. The ratio of dimer to trimer and heavies was thus 6.94:1. The TGA indicated that the material was definitely too volatile; 82.1% sample remaining.

EXAMPLE 29

Oligomerization

Oligomerization of a 70% $C_{14}$ internal olefin—30% $C_8$ alpha olefin mixture catalyzed by 2.5 g $BF_3$ and 1.1 g 1-butanol as promoter was conducted starting at 75.1° C. To a clean and dry 300 ml clave were added 119 g of $C_{14}$ internal olefin and 51 g of $C_8$ alpha olefin of the same sources as the previous two examples, followed by 1.1 g of 1-butanol promoter. The clave was sealed and heated to 75.1° C. and at that temperature $BF_3$ gas was added in increments (shots) over a 10 minute period. Five separate shots were applied to total 2.5 g. Eleven minutes after the first $BF_3$ addition, the reaction temperature had risen to 100.7° C. (a maximum exotherm of 25.6° C.). The reaction was held at 75° C. for 1.5 hours total and then cooled and worked up as in the previous examples. The dry product from this lower temperature oligomerization had the following liquid chromatography analysis: 12.7% of monomer ($C_8$, $C_{14}$ and $C_{16}$), 23.7% of $C_{22}$, 42.1% of $C_{28}$ and 21.4% of trimer and heavies. Conversion to materials greater than $C_{16}$ was 87.3% with the dimer to trimer and heavies being 3.07:1.

Hydrogenation and Stripping

Hydrogenation of the oligomer from the above step was completed at 210° C., 4.0 hours and 2,000 psig hydrogen pressure. Workup (filtration) followed by high vacuum stripping afforded a bottoms product which amounted to 70.7% of the charge and had the following properties: 210° F. viscosity of 4.16 cs, 25° C. viscosity of 34.5 cs, pour point of $<-50°$ F. and a viscosity index of 124.2. The liquid chromatography analysis indicated 16.7% of the material was $C_{22}$, 56.8% was $C_{28}$ and 26.5% was heavies. TGA indicated the sample had excellent volatility (90% remaining at 233° C.).

EXAMPLES 30-38

Examples 30-35 were conducted in a manner similar to Examples 27-29 except that certain parameters were changed as shown in Table III.

Examples 36-38 were conducted according to the following procedure. Eightly-three grams of delta 7 $C_{14}$ and 36 g of delta 9 $C_{18}$ internal olefin and 51 g of $C_8$ alpha olefin were added to a 300 ml Hastelloy clave followed by 1.1 g of 1-butanol. This olefin mixture is the closest approximation to the U.S. Pat. No. 4,300,006 feedstocks obtainable with the materials on hand. The clave was sealed and $BF_3$ introduced in the indicated quantities. Workup was conducted as usual involving an aqueous $Na_2CO_3$ wash followed by two water washes and filtering the organic layer through filter paper to dry it. Hydrogenation was accomplished at 210° C. and in the presence of 5% (by weight, basis olefin) nickel catalyst and 2,000 psig hydrogen pressure for four hours. The hydrogenation product was filtered and distilled at high vacuum ($<0.1$ mm Hg) and to a head temperature of 110° C. The bottoms product was submitted for analysis. The results of this last set of comparative examples are summarized in Table III.

TABLE III

EXPERIMENTS USING LOWER MOLECULAR WEIGHT ALPHA AND HIGHER MOLECULAR WEIGHT INTERNAL OLEFINS AS FEEDSTOCKS

| Ex. | Feedstock, wt. % Internal | Feedstock, wt. % Alpha | Reaction Temp., °C. | Reaction Time, Hours | BF$_3$ Added Grams | Maximum Exotherm, °C. | Liquid Chromatography Conv. | Liquid Chromatography Dimer, Trimer and Heavies | % Bottoms | Properties of Hydrogenated Stripped Oligomers Centistokes, 210° F. | Properties of Hydrogenated Stripped Oligomers Centistokes, 25° C. | VI | Pour Point, °F. | TGA |
|---|---|---|---|---|---|---|---|---|---|---|---|---|---|---|
| 27 | 70 C$_{14}$ | 30 C$_8$ | 95.1–110.2 | 1.0 | 2.5 | 15.1 | 68.1 | 7.19:1 | 49.6 | 3.80 | 27.4 | 110.0 | <−50 | 85.0 |
| 28 | 70 C$_{14}$ | 30 C$_8$ | 94.9–110.0 | 1.0 | 2.2 | 15.1 | 68.9 | 7.30:1 | 55.3 | 3.45 | 25.7 | 109.0 | −40 | 82.1 |
| 29 | 70 C$_{14}$ | 30 C$_8$ | 75.1–100.7 | 1.5 | 2.5 | 25.6 | 87.3 | 3.07:1 | 70.7 | 4.16 | 34.5 | 124.2 | <−50 | 90.0 |
| 30 | 70 C$_{14}$ | 30 C$_8$ | 75.0–96.4 | 1.5 | 2.5 | 21.9 | 93.5 | 1.55:1 | — | — | — | — | — | 86.0 |
| 31 | 48.8 Δ7 C$_{14}$ + 21.2 Δ9 C$_{18}$ | 30 C$_8$ | 75.1–97.4 | 1.5 | 2.1 | 22.3 | 83.1 | — | 83.5 | 3.41 | 24.3 | 108.9 | +20 | 76.4 |
| 32 | 70 C$_{14}$ | 30 C$_8$ | 25.0–47.8 | 1.5 | 2.6 | 22.8 | 82.0 | 3.74:1 | 81.9 | 4.91 | 40.8 | 138.6 | −15 | 92.9 |
| 33 | 70 C$_{14}$ | 30 C$_8$ | 25.0–28.1 | 6.5 | 2.4 | 3.1* | 21.4 | 6.38:1 | 15.5 | — | — | — | — | 83.8 |
| 34 | 70 C$_{14}$ | 30 C$_8$ | 25.0–54.5 | 1.5 | 5.4 | 29.4 | 96.9 | 0.93:1 | 93.5 | 4.99 | 45.0 | 125.6 | −35 | 92.0 |
| 35 | 70 C$_{14}$ | 30 C$_8$ | 25.0–55.8 | 6.5 | 5.4 | 30.7 | 97.3 | 0.65:1 | 92.8 | 5.91 | 58.4 | 126.9 | −45 | 93.6 |
| 36 | 48.8 Δ7 C$_{14}$ + 21.1 Δ9 C$_{18}$ | 30 C$_8$ | 25.2–44.4 | 1.5 | 2.5 | 19.2 | 86.1 | — | 72.0 | 4.40 | 37.1 | 120.3 | <−50 | 90.3 |
| 37 | 48.8 Δ7 C$_{14}$ + 21.1 Δ9 C$_{18}$ | " | 25.1–41.7 | 1.5 | 5.1 | 21.6 | 93.1 | — | 85.0 | 4.67 | 39.2 | 123.6 | <−50 | 90.0 |
| 38 | 48.8 Δ7 C$_{14}$ + 21.1 Δ9 C$_{18}$ | " | 25.1–51.1 | 6.5 | 5.5 | 26.0 | 96.4 | — | 85.2 | 5.63 | 54.0 | 123.2 | −40 | 94.0 |

*This reaction never started.

As can be seen from Table III, the product from the feedstocks used in U.S. Pat. No. 4,300,006 are unsuitable for use as a synthetic lubricant without further distillation; i.e., the bottoms product found useful using the internal olefin feedstocks of the invention are superior. Examples 32–38 have 210° F. and 25° C. viscosities which are too high for use as 4 cs synthetic lubricants. One skilled in the art would not expect these materials to pass cold cranking tests. These same feedstocks, when run at a higher temperature, produce a material with a low viscosity index and a poor TGA value (see Example 31).

Thus, it is determined by comparative examples using the conditions of U.S. Pat. No. 4,300,006 that the resulting products would need to be distilled in order to meet the 4.0 cs 210° F. viscosity requirement and apparently the cold cranking specifications as well.

The oligomer mixtures produced from C$_{13-14}$ internal olefins via a promoted BF$_3$ catalyst have proven to be exceptional synthetic lubricant additives. As these mixtures have a 210° F. viscosity of about four centistokes, they are considered "4 cs" fluids. A typical fluid of this invention was compared with the commercially available 4 cs fluid from Gulf Oil Chemicals Co. It should be emphasized that the synthetic lubricant components of the instant invention are preferably used without further distillation after the monomer removal and hydrogenation steps. In other words, the undistilled bottoms are the finished synthetic lubricant component. The Gulf fluids must be distilled into "2 cs," "4 cs," "6 cs," etc. fractions before they can be useful. Thus, the method of this invention does not require a costly distillation step, which is an important advantage over methods used by others in the field. Comparison of the properties of the fluids themselves are given in Table IV. It may be seen that the fluid of this invention (A) is somewhat less viscous than the Gulf fluid (B) at the higher temperatures, though it is somewhat more viscous at the lower temperatures. The viscosity index for fluid A is somewhat less than for fluid B, but they are generally comparable.

TABLE IV

PHYSICAL PROPERTIES OF 4 cs FLUIDS

| TESTS | °C. | °F. | A* | B |
|---|---|---|---|---|
| Kinematic Viscosity, cs at | 150.0 | 302.0 | 1.82 | 1.96 |
|  | 100.0 | 212.0 | 3.72 | 3.94 |
|  | 98.9 | 210.0 | 3.79 | 4.02 |
|  | 40.0 | 104.0 | 16.36 | 17.11 |
|  | 37.8 | 100.0 | 17.70 | 18.49 |
| Brookfield Viscosity, centipoise at | −28.9 | −20.0 | 800 | 780 |
|  | −40.0 | −40.0 | 2340 | 2200 |
| Viscosity Index |  |  | 115 | 128 |
| Viscosity, Injector Shear Stability, % Change at | 100.0 | 212.0 | +1.9 | +0.5 |
|  | 98.9 | 210.0 | +1.9 | +0.5 |
|  | 40.0 | 104.0 | +2.8 | +1.1 |
|  | 37.8 | 100.0 | +4.5 | +1.1 |
| Pour Point, °F. |  |  | <−65 | <−65 |
| Cloud Point, °F. |  |  | −56 | −54 |
| Specific Gravity, 60/60, °F. |  |  | 0.8213 | 0.8199 |
| Gravity, °API |  |  | 40.8 | 41.1 |

*A = Fluid of this invention
B = Gulf fluid

A measure of the volatility of the two fluids is presented in Table V where it may be seen that oligomer A is more volatile than fluid B.

TABLE V

| SIMULATED DISTILLATION | | |
|---|---|---|
| Weight % Off at °F. | A | B |
| Initial Boiling Point | 689 | 613 |
| 2 | 702 | 717 |
| 4 | 717 | 759 |
| 6 | 722 | 769 |
| 8 | 726 | 774 |
| 10 | 729 | 777 |
| 15 | 737 | 783 |
| 20 | 743 | 787 |
| 25 | 749 | 790 |
| 50 | 788 | 807 |

Two motor oils were formulated having the same proportions of the same components, except that formulation A had 35 wt.% of a 4 cs fluid of this invention and formulation B had 35 wt.% of the Gulf 4 cs fluid. The rest of the components of the two formulations are identical in type and proportion and include materials such as mineral oils, dispersants, antioxidants, detergents, friction modifiers, rust inhibitors, viscosity index improvers, pour point depressants and antifoamants. The proportion of 35 wt.% is large enough for the additives to have a profound effect on the behavior of the formulations in testing. The properties of the motor oil formulations are given in Table VI.

The results of the engine tests of the two formulations are presented in Table VII. The engine tests run on the two formulations are standard tests well known to those skilled in the art.

TABLE VI

| PROPERTIES OF MOTOR OIL FORMULATIONS | | | |
|---|---|---|---|
| | A | B | API SW 30 Grade Limits |
| Kin. vis. at 100° C., cs | 9.48 | 9.54 | 9.3 to 12.5 |
| CCS vis. at −25° C., cP | 3500 | 3450 | 3500 max. |
| MBPT, °C. | −34.7 | −34.1 | −30 max. |
| Pour Point | −40 | −45 | |

TABLE VII

| ENGINE TEST RESULTS | | | |
|---|---|---|---|
| TESTS | A | B | API SF/CC GRADE LIMITS |
| SEQ IIID TEST Oxidation Stability Test | | | |
| Vis. Inc.[1], % at 64 Hr. | 28 | 242 | 375 max. |
| Sludge | 9.6 | 9.6 | 9.2 min. |
| Varnish | 9.2 | 9.2 | 9.2 min. |
| ORLD[2] | 8.0 | 7.1 | 4.8 min. |
| C+L[3] Wear | | | |
| Average, inch | 0.0021 | 0.0011 | 0.0040 max. |
| Maximum, inch | 0.0035 | 0.0027 | 0.0080 max. |
| Ring Sticking | None | None | None |
| Lifter Sticking | None | None | None |
| Cam +/or Lifter Scuffing | None | None | None |
| Oil Consumption, quarts | 5.0 | 6.47 | 6.38 max. |
| CRC L-38 TEST Bearing Corrosion | | | |
| BWL[5], mg | 24.3 | 45.9, 39.5 | 40.0 max. |
| CAT 1H-2 TEST Diesel Piston Deposits Test | | | |
| 120 Hour TGF[6], % | 13.0 | 4.0 | |
| WTD[7] | 25.6 | 71.9 | |
| 480 Hour TGF, % | 15.5 | 5.0 | 45 max. |
| WTD | 96.5 | 137.1 | 140 max. |

[1]Viscosity increase
[2]Oil ring land deposits
[3]Cam and Lifter
[4]Piston Skirt Varnish
[5]Bearing Weight Loss
[6]Top Groove Filling
[7]Weighted Total Demerits Sequence IIID tests are oxidation stability tests designed to measure the wear protection characteristics; that is, to measure how the oils protect internal loaded engine components against excessive wear. The engine is run at high speed under high loads. The first measurement is the percent increase in 40° C. viscosity after 64 hours. It is surprising to note that formulation A had a much lower viscosity change than did formulation B when it is remembered that oligomer mixture B had a higher viscosity index (indicating less change of viscosity with temperture) than did oligomer mixture B (see Table IV). What is also surprising is that formulation B required 6.47 quarts of oil for the Sequence IIID tests, whereas formulation A required only 5.0 quarts. This result is contrary to what would be expected from the volatility information derived from the simulated distillation set out in Table V. It is particularly surprising when it is realized that the 4 cs fluid of this invention comprises only about 25% heavies. One skilled in the art would expect the more volatile material (A) to cause any formulation made therefrom to require more oil. However, as may be seen in Table VII, it is formulation B, having the less volatile oligomer mixture, which has the greater quantity requirements.

In the rest of the sequence IIID tests, the two formulations were quite comparable. However, formulation A again gives better results in the Coordinating Research Council L-38 test, which is a measure of bearing corrosion by measuring the weight loss of the bearing. In the first determination, formulation B failed the test with a weight loss of 45.9 mg, though it passed on a second attempt with 39.5 mg loss. Formulation A caused a much lower weight loss of 24.3 mg.

The Caterpillar 1H2 test is test measuring the accumulation of deposits on diesel pistons, among other criteria. Demerits are assigned in this test by the subjective opinion of a person approved by API (American Petroleum Institute). Although formulation A performed poorer than formulation B in the amount of top groove filling found, the weighted total demerits for both durations for formulation A was much less than that for formulation B. These results are further evidence of the surprisingly superior characteristics of the oligomer mixtures made from only internal olefins and a promoted BF$_3$ catalyst.

In summary, the invention encompasses a unique first step of transforming predominantly propylene and/or n-butenes alone to higher internal olefins through the application of not one but two known chemical unit processes: isomerization and disproportionation. More important is the fact that the procedure taught here is unique because it reveals an overall process for the manufacture of synthetic lubricants derived from the C$_9$–C$_{14}$ olefins from the isomerization/disproportionation step. These synthetic lubricants have unexpectedly low viscosities and display performance equal or superior to that shown by the current industry standard: hydrogenated polydecene-1. Thus, the approach of this process provides for superior quality synthetic lubricants which have previously been unavailable from feedstocks such as propylene and/or n-butenes.

Many modifications may be made in the method of this invention without departing from its scope which is defined only by the appended claims. For example, it would be expected that one skilled in the art could change the cocatalysts, the $BF_3$ promoter, the temperature, pressure, modes of addition or the olefin molecular weight in trying to maximize the conversion or the oligomer properties, such as to make a 6 cs fluid, for example.

We claim:

1. A process for converting $C_3$–$C_4$ linear olefins to a synthetic lubricant component comprising
   a. isomerizing a linear olefin feedstock selected from the group of olefins consisting of propylene, butene-1, butene-2 and mixtures thereof, over a heterogeneous isomerization catalyst selected from the group of catalysts consisting of cobalt oxide, iron oxide and manganese oxide, each of which is supported on alumina, and sodium and potassium carbonate supported on gamma alumina, at a temperature of about 70° C.,
   b. disproportionating the mixture resulting from the isomerization step by passing the mixture over a heterogeneous disproportionation catalyst selected from the group of catalysts consisting of molybdenum, tungsten and rhenium, each of which is supported on alumina, and a mixture of molybdenum and cobalt supported on alumina, at a temperature in the range of about 100° to 175° C. and at a pressure of greater than 200 psig,
   c. separating from the mixture resulting from the disproportionation step a mixture of olefins having carbon numbers ranging from 9 to 24, and being comprised of 99 weight percent or more internal olefins,
   d. oligomerizing the mixture of internal olefins separated in the previous step by contacting the mixture with a catalyst comprising boron trifluoride and a protonic promoter being selected from the group of promoters consisting of alcohols, carboxylic acids and water, at a temperature between about 25° and about 150° C.,
   e. mildly stripping off any unreacted olefin monomers from the mixture of oligomerized olefins resulting from the oligomerization step, and
   f. hydrogenating the oligomerized olefins from the previous step in the presence of hydrogen and a hydrogenation catalyst to produce a synthetic lubricant component.

2. The process of claim 1 in which the part of the mixture remaining after separation of the internal olefins in step (c) is recycled to the disproportionation step.

3. The process of claim 1 in which the internal olefins of a carbon number ranging from 9 to 24 separated in step (c) have the double bond of the olefin randomly distributed throughout the carbon chain.

4. The process of claim 1 in which the promoter is 1-butanol.

5. The process of claim 1 in which the unreacted olefin monomers stripped off in step (e) are recycled to the oligomerization step.

6. The process of claim 1 in which the mild stripping step is conducted at a temperature between 160° and 180° C.

7. The process of claim 1 in which the hydrogenation catalyst used in step (f) is selected from the group of hydrogenation catalysts consisting of nickel-copper-chromium and cobalt-copper-chromium.

8. The process of claim 1 in which the internal olefins separated out in step (c) have 13 or 14 carbon atoms or a mixture thereof and the synthetic lubricant component resulting from step (f) has a viscosity at 210° F. of between 3.5 and 5.0 centistokes, a viscosity at 25° C. of between 25 and 40 centistokes, a viscosity index of greater than 100 and a thermogravimetric analysis value of greater than 80 weight percent.

9. A process for converting $C_3$–$C_4$ linear olefins to a synthetic lubricant component comprising
   a. isomerizing a linear olefin feedstock selected from the group of olefins consisting of propylene, butene-1, butene-2 and mixtures thereof, over a heterogeneous isomerization catalyst selected from the group of catalysts consisting of cobalt oxide, iron oxide and manganese oxide, each of which is supported on alumina and sodium and potassium carbonate supported on gamma alumina, at a temperature of about 70° C.,
   b. disproportionating the mixture resulting from the isomerization step by passing the mixture over a heterogeneous disproportionation catalyst selected from the group of catalysts consisting of molybdenum, tungsten and rhenium, each of which is supported on alumina and a mixture of molybdenum and cobalt supported on alumina, at a temperature in the range of about 100° to 175° C. and at a pressure of greater than 200 psig,
   c. separating from the mixture resulting from the disproportionation step a mixture of olefins having carbon numbers ranging from 9 to 24, and being comprised of 99 weight percent or more internal olefins,
   d. oligomerizing the mixture of internal olefins separated in the previous step by contacting the mixture with a catalyst system comprising boron trifluoride and a protonic promoter being selected from the group of promoters consisting of alcohols, carboxylic acids and water, at a temperature between about 25° and about 150° C.,
   e. mildly stripping off any unreacted olefin monomers from the mixture of oligomerized olefins resulting from the oligomerization step, at a temperature between 160° and 180° C. and recycling the monomers to the oligomerization step as the only separation step, and
   f. hydrogenating the oligomerized olefins from the previous step in the presence of hydrogen and a hydrogenation catalyst to produce a synthetic lubricant component having a viscosity at 210° F. of between 3.5 and 5.0 centistokes, a viscosity at 25° C. of between 25 and 40 centistokes, a viscosity index of greater than 100 and a thermogravimetric analysis value of greater than 80 weight percent.

10. The process of claim 9 in which the internal olefins separated in step (c) have the double bond of the olefin randomly distributed throughout the carbon chain, and the part of the mixture remaining after separation of the internal olefins is recycled to the disproportionation step.

11. The process of claim 9 in which the protonic promoter of the oligomerization step is 1-butanol.

12. The process of claim 9 in which the hydrogenation catalyst used in the last step is selected from the group of hydrogenation catalysts consisting of nickel-copper-chromium and cobalt-copper-chromium.

13. The process of claim 9 in which the internal olefins separated in step (c) have 13 or 14 carbon atoms or mixtures thereof.

14. A process of converting $C_3$–$C_4$ linear olefins to a synthetic lubricant component comprising
   a. isomerizing a linear olefin feedstock selected from the group of olefins consisting of propylene, butene-1, butene-2 and mixtures thereof, over a heterogeneous isomerization catalyst selected from the group of catalysts consisting of cobalt oxide, iron oxide and manganese oxide, each of which is supported on alumina and sodium and potassium carbonate supported on gamma alumina, at a temperature of about 70° C.,
   b. disproportionating the mixture resulting from the isomerization step by passing the mixture over a heterogeneous disproportionation catalyst selected from the group of catalysts consisting of molybdenum, tungsten and rhenium, each of which is supported on alumina and a mixture of molybdenum and cobalt supported on alumina, at a temperature in the range of about 100° to 175° C. and at a pressure of greater than 200 psig,
   c. separating from the mixture resulting from the disproportionation step a mixture of olefins having carbon numbers ranging from 9 to 24, and being comprised of 99 weight percent or more internal olefins and having the double bond randomly distributed throughout the carbon chain, the remainder being recycled to the disproportionation step,
   d. oligomerizing the mixture of internal olefins separated in the previous step by contacting the mixture with a catalyst system comprising boron trifluoride and a protonic promoter being selected from the group of promoters consisting of alcohols, carboxylic acids and water, at a temperature between about 25° and about 150° C.,
   e. neutralizing the crude oligomer product from the previous step,
   f. removing the organic layer from the neutralized crude product,
   g. mildly stripping off any unreacted olefin monomers from the mixture of oligomerized olefins in the organic layer from the previous step, at a temperature between 160° and 180° C. and recycling the monomers to the oligomerization step, as the only separation step, and
   h. hydrogenating the oligomerized olefins from the previous step in the presence of hydrogen and a hydrogenation catalyst to produce a synthetic lubricant component having a viscosity at 210° F. of between 3.5 and 5.0 centistokes, a viscosity at 25° C. of between 25 and 40 centistokes, a viscosity index of greater than 100 and a thermogravimetric analysis value of greater than 80 weight percent.

15. The process of claim 14 in which the protonic promoter in the oligomerization step is 1-butanol.

16. The process of claim 14 in which the internal olefins separated in step (c) have 13 or 14 carbon atoms or mixtures thereof.

17. The process of claim 14 in which the hydrogenation catalyst of the last step is selected from the group of hydrogenation catalysts consisting of nickel-copper-chromium and cobalt-copper-chromium.

* * * * *